US005180852A

United States Patent [19]

Shaw

[11] Patent Number: 5,180,852

[45] Date of Patent: Jan. 19, 1993

[54] PREPARATION OF BIS(ORGANOTHIO) ALKANES

[75] Inventor: James E. Shaw, Bartlesville, Okla.

[73] Assignee: Phillips Petroleum Company, Bartlesville, Okla.

[21] Appl. No.: 837,839

[22] Filed: Feb. 19, 1992

Related U.S. Application Data

[62] Division of Ser. No. 767,592, Sep. 30, 1991, Pat. No. 5,132,008.

[51] Int. Cl.[5] .......... C07C 319/18

[52] U.S. Cl. .......... 568/57

[58] Field of Search .......... 568/57

[56] References Cited

U.S. PATENT DOCUMENTS 2,125,337 8/1938 Gaudin et al. .......... 209/166

3,032,593 5/1962 Schneider .......... 568/57

4,681,675 7/1987 Bresson et al. .......... 209/167

OTHER PUBLICATIONS

J. Org. Chem. 50:4390, by Caserio et al. (1985).

*Primary Examiner*—Marianne M. Cintins

*Assistant Examiner*—Michael B. Hydorn

*Attorney, Agent, or Firm*—Lucas K. Shay

[57] ABSTRACT

A bis(organothio) alkane, such as 1,2-bis(methylthio) hexane, is synthesized by reacting an alkene, such as 1-hexene, with an excess amount of a disulfide thiolating agent, such as dimethyl disulfide, in the presence of a catalytic amount of a catalyst, such as a boron trifluoride dialkyl etherate. The reaction can be carried out at from about 20° to about 150° C. and under a pressure of from about 0 to 20 atms. The bis(organothio) alkane is useful in ore flotation process as a flotation agent for ores containing metal sulfide minerals.

18 Claims, No Drawings

PREPARATION OF BIS(ORGANOTHIO) ALKANES

This application is a division of application Ser. No. 07/767,592, filed Sep. 30, 1991, now U.S. Pat. No. 5,132,008.

FIELD OF THE INVENTION

This invention relates to a method for preparing bis-(organothio) alkanes. In another embodiment it relates to recovering minerals from sulfide ores.

BACKGROUND OF THE INVENTION

Froth flotation is a process for concentrating minerals from ores. In a froth flotation process, the ore is crushed and wet ground to obtain a pulp. Additives such as mineral flotation or collecting agents and frothing agents are added to the pulp to assist in subsequent flotation steps and the valuable minerals are separated from the undesired, or gangue, portions of the ore. After flotation agents are added, the pulp is aerated to produce a froth. The minerals which adhere to the bubbles of froth are skimmed or otherwise removed and the mineral-laden froth is collected and further processed to further concentrate and purify the desired minerals.

Generally the ore is initially floated to produce a rougher concentrate, the rougher concentrate thereafter being refloated, sometimes in the presence of depressants, to further separate the minerals therein. Typical mineral flotation collectors include xanthates, amines, alkyl sulfates, arenes, sulfonates, dithiocarbamates, dithiophosphates, fuel oil and thiols.

It is a continuing goal in the ore-processing industry to increase the productivity of ore flotation processes and, above all, to provide specific procedures which are selective to one mineral over other minerals present in the treated material.

A bis(organothio) alkane can be produced by boron trifluoride etherate-catalyzed addition of dialkyl disulfide to alkenes (See J. Org. Chem. 50:4390, 1985). However, the reference teaches the use of excess alkenes in a solvent mixture of dichloromethane and nitromethane. Though the reference shows reasonably good yield when alkenes other than 1-alkenes are used, the yield is very poor with 1-alkenes. For example, when excess 3-methyl-1-butene is used to prepare a 1,2-bis(methylthio)-3-methylbutane, the yield is only 5%.

SUMMARY OF THE INVENTION

It is therefore an object of this invention to provide compounds suitable as flotation agents for metal sulfide minerals for use in ore flotation processes.

It is also an object of this invention to provide compounds useful for extracting metals from metal containing mixtures.

It is another object of this invention to provide a method for recovering metal sulfide minerals from their ores using ore flotation process.

It is still another object of this invention to provide an improved method for preparing ore flotation compounds for recovering the minerals.

It is a further object of this invention to provide a method for using the ore flotation compounds for the recovery of minerals in a flotation process.

It is yet another object of this invention to provide a method for preparing the ore flotation compounds in high yield.

Other aspects, objects and the various advantages of this invention will become apparent upon reading this specification and the appended claims.

According to this invention, a process for recovering metals from ores comprises admixing an ore containing metal sulfide minerals, in a froth flotation process, with a bis(organothio) alkane having the formula of RCH(SR")CH(SR")R' in an amount sufficient to aid in the flotation of the minerals to form a flotation slurry so that the minerals can be recovered from the flotation slurry wherein R is an alkyl group, R' is independently a hydrogen or an alkyl group, and R" is an alkyl or aryl group.

In another embodiment of this invention, a process for preparing the bis(organothio) alkane comprises contacting an alkene having the formula of RCH═CHR' with an excess amount of a thiolating agent having the formula of R"SSR" in the presence of a catalyst, wherein the R is an alkyl group, R' is independently a hydrogen or an alkyl group and R" is an alkyl or aryl group.

DETAILED DESCRIPTION OF THE INVENTION

According to the present invention, a process for the recovery of minerals from particulate solids containing minerals comprises first mixing the solids with water and a bis(organothio) alkane to establish a pulp, then aerating the pulp to produce a froth containing the minerals, and finally recovering the minerals from the froth.

The particulate solids containing minerals can be any metal sulfide bearing ores. Some suitable ores are covallite (CuS), chalcocite ($Cu_2S$), chalcopyrite ($CuFeS_2$), bornite ($Cu_5FeS_4$), cubanite ($Cu_2SFe_4S_5$), valeriite ($Cu_2Fe_4S_7$) or ($Cu_3Fe_4S_7$), enargite ($Cu_3AsS_4$), tetrahydrite ($Cu_3SbS_2$), tennanite ($Cu_{12}As_4S_{13}$), stibnite ($Sb_2S_3$), sphalerite (ZnS), molybdenite ($MoS_2$), argentite ($Ag_2S$), stephanite ($Ag_5SbS_4$), daubreelite ($FeSCr_2S_3$), cooperite ($Pt(AsS)_2$), stannite ($Cu_3FeSSnS_2$), pentlandite ($(Fe, Ni)_9S_8$), and Teallite ($TeSnS_2$), and the like.

Any froth flotation apparatus can be used in this invention. The commonly used commercial flotation machines are the Agitair (Gallagher Company), Denver (Denver Equipment Company), and the Fagergren (Western Machinery Company). Smaller, laboratory scale apparatus such as a Hallimond cell, can also be used.

The instant invention has been demonstrated in tests conducted at ambient room temperature and atmospheric pressure. However, any temperature or pressure generally employed by those skilled in the art are within the scope of this invention.

The bis(organothio) alkanes useful in the practice of the invention can be bis(alkylthio) alkanes or bis(arylthio) alkanes. The bis(alkylthio) alkanes have the formula of RCH(SR")CH(SR")R' wherein R is an alkyl group having 1 to 20 carbon atoms, R' is independently a hydrogen or a $C_1$–$C_{10}$ alkyl group, and R" is an alkyl group having about 1 to 10 carbon atoms. Examples of the bis(alkylthio) alkanes include 1,2-bis(methylthio) hexanes, 1,2-bis(methylthio) octane, 1,2-bis(benzylthio) hexane, 1,2-bis(methylthio)cyclohexane, and the like.

The bis(arylthio) alkanes useful in the present invention have the formula of RCH(SR")CH(SR")R' wherein R is an alkyl group having 1 to 20 carbon atoms, R' is independently a hydrogen or an alkyl group having 1 to 10 carbon atoms, and R" is an aryl group having 6 to 10 carbon atoms. The aryl group can be unsubstituted or substituted with one or more substituents including $C_1$–$C_4$ alkyl, halo, or $OR_1$ wherein $R_1$ is $C_1$–$C_4$ alkyl. An example of suitable bis(arylthio) alkane is 1,2-bis(phenylthio) hexane.

The amount of bis(alkylthio) or bis(arylthio) alkane employed in the flotation process of this invention is not critical. The quantity employed will depend upon numerous variables, including the particular ore being treated, the concentration of the desired minerals in the ore being treated and the process parameters of the flotation process employed. Generally, the flotation compounds of the present invention can be employed in the ore flotation mineral recovery process at a concentration level sufficient to provide the desired flotation action on certain minerals. The amount of bis(organothio) alkane employed as a flotation agent in the mineral recovery process of the present invention will generally range from about 0.005 pounds to about 10 pounds per ton of solids or crushed ore. More preferably, the amount of bis(organothio) alkane employed will range from about 0.02 to about 2 pounds per ton of solids or crushed ores. The flotation compounds employed in the practice of the present invention can be added to an ore flotation mineral recovery process or system at the ore-grinding stage, an intermediate conditioning step, the ore flotation step and/or to the concentrate which is to be further floated.

According to another embodiment of the present invention, a process for preparing the bis(organothio) alkanes comprises contacting an alkene with an excess amount of a thiolating agent in the presence of a suitable catalyst.

The bis(organothio) alkanes useful in the practice of this embodiment of the present invention can also be bis(alkylthio) alkanes or bis(arylthio) alkanes. The bis(alkylthio) alkanes have the formula of RCH(SR")CH(SR")R' wherein R is an alkyl group having 1 to 20 carbon atoms, R' is independently a hydrogen or a $C_1$–$C_{10}$ alkyl group, and R" is an alkyl group having about 1 to 10 carbon atoms. Examples of the bis(alkylthio) alkanes include 1,2-bis(methylthio) hexane, 1,2-bis(methylthio) octane, 1,2-bis(ethylthio) hexane, 1,2-bis(methylthio) decane, and other bis(alkylthio) alkanes.

The bis(arylthio) alkanes useful in the present invention have the formula of RCH(SR")CH(SR")R' wherein R is an alkyl group having 1 to 20 carbon atoms, R' is independently a hydrogen or an alkyl group having 1 to 10 carbon atoms, and R" is an aryl group having 6 to 10 carbon atoms. The aryl group can be unsubstituted or substituted with one or more substituents including $C_1$–$C_4$ alkyl, halo, or $OR_1$ wherein $R_1$ is $C_1$–$C_4$ alkyl. Examples of bis(arylthio) alkanes are 1,2-bis(phenylthio) octane, and other bis(arylthio) alkanes.

The alkenes useable in this invention are those having only one double bond and having 2 to 22 carbon atoms. Preferably the alkenes have the double bond at the first carbon atom. Suitable alkenes include ethylene, propylene, 1-butene, 1-pentene, 1-hexene, 1-heptene, 1-octene, and other 1-alkenes.

Thiolating agents useful in this invention include dialkyl disulfide and diaryl disulfide having the formula of R"SSR" wherein R" is an alkyl or aryl group having 1 to 20 carbon atoms. The thiolating agents are liquid in nature under ambient conditions. Examples of suitable dialkyl disulfides include dimethyl disulfide, diethyl disulfide, dipropyl disulfide, and other dialkyl disulfides. Diaryl disulfides include those whose aryl group is unsubstituted or substituted with one or more substituents including $C_1$–$C_4$ alkyl, halo, or $OR_1$ wherein $R_1$ is $C_1$–$C_4$ alkyl. Examples of suitable diaryl disulfides are diphenyl disulfide, ditolyl disulfide, and other diaryl disulfides.

The catalyst suitable for the thiolating reaction of alkenes is selected from the group consisting of boron trichloride, boron tribromide, boron trifluoride, aluminum chloride, and a boron trifluoride dialkyl etherate. The preferred catalyst is a boron trifluoride dialkyl etherate. Examples of suitable boron trifluoride dialkyl etherate include boron trifluoride dimethyl etherate, boron trifluoride diethyl etherate, and other boron trifluoride dialkyl etherates. Boron trifluoride diethyl etherate is most preferred because it is soluble in the reaction mixture of this embodiment of the present invention.

The mole ratio of the thiolating agent to alkene operable in the present invention is about 1.2 to about 10.0, preferably about 1.2 to about 5.0 and most preferably about 1.5 to about 3.0 in order to obtain a high yield of the bis(organothio) alkanes.

The thiolating reaction of the alkenes and thiolating agents can be carried out at any temperature or pressure generally employed by those skilled in catalytic reactions. However, it is preferred that the reaction be carried out from about 20° to about 150° C. and from about 0 to about 20 atms, and more preferably 50° to 100° C. and 1 to 5 atms for better control of the reaction and better product yield.

The bis(organothio) alkanes can be recovered, if needed, by any suitable means employed by those skilled in the art. For example, phase separation can be initiated by adding a caustic solution to the reaction mixture to neutralize HF generated from boron trifluoride and water followed by recovering the desired product.

EXAMPLE I

This example describes the procedure used to evaluate the bis(alkylthio) or bis(arylthio) alkanes in an ore flotation process and demonstrates their usefulness as flotation agents. The basic procedures followed are well known by those skilled in the art.

One kilogram (previously crushed such that 100% passed through a 10 mesh U.S. Standard Sieve (2.00 mm), (Tyler #9 equivalent)) of a Cu/Zn/Fe containing ore, 650 ml of deionized water, and 0.5 g (500 g/metric ton) of lime (CaO) were added to a ball mill. This addition of lime was found too sufficient to achieve a pH of near 9.3 in the resultant slurry. The slurry was ground for 25 minutes 40 seconds achieving a grind such that 62% passed through a 200 mesh U.S. Standard (200 mesh Tyler equivalent) (75 micron) sieve. The ground mixture was transferred to a 2.5 liter capacity Denver D-12 flotation cell. Sufficient deionized water was added during the transfer to raise the level in the cell to approximately 2.5 cm below the cell lip. The aqueous slurry thus contained approximately 30% by weight solids.

The flotation machine was turned on (previously adjusted to operate at 1800 rpm) mixing and agitating the slurry. The pH of the slurry measured and adjusted to 9.3 as required. Sodium sulfite (152 g/mt) was added to depress the zinc mineral, predominantly sphalerite, during the copper flotation stages.

The copper mineral collector for the control was a commercial collector produced by Cyanamid Inc. and marketed under the designation 3418A. The zinc mineral collector for the control was sodium isopropyl xanthate (SIPX). The frother was methyl isobutyl carbinol (MIBC).

A 2 minute conditioning stage was used in the flotation procedure. Prior to the start of the conditioning stage 0.031 g (3.1 ml of 1% solution) (31 g/mt) of 3418A and 0.009 g (9 g/mt) of MIBC were added.

Air was introduced into the process at the end of the 2 minute conditioning time. Additional DI water was added as required during the flotation periods. The mineral laden froth (concentrate) was removed from the flotation cell for a time period of 7 minutes. The concentrate was collected as 2 fractions with the 1st fraction consisting of the concentrate from the 1st 2 minutes of flotation time and the second fraction consisting of the concentrate from the remaining 5 minutes. These 2 fractions comprised the copper concentrates.

The air introduction was stopped after the 7 minutes of flotation time, addition makeup water was added as required and the pH adjusted to 10.7 with lime water. Copper sulfate, 0.65 g (3.2 ml of 20% solution) (646 g/mt) was added and the slurry allowed to condition 2 minutes. Following this conditioning stage 0.059 g (5.9 ml of 1% solution) (59 g/mt) of SIPX, 0.006 g (6 g/mt) of MIBC were added and the slurry allowed to condition an additional 2 minutes.

Air was introduced back into the process and the concentrate removed for 8 minutes. The concentrate was again collected in fractions with the first fraction consisting of the concentrate from the first 2 minutes of flotation time and the second fraction consisting of the concentrate from the remaining 6 minutes of flotation time.

Again the air introduction was stopped. Additional SIPX (1 ml of 1% solution (10 g/mt)) and MIBC (0.003 g (3 g/mt)) were added to the slurry and the slurry conditioned for 1 minute.

Air was introduced into the process again and the concentrate removed for a 3 minute period. This concentrate was the 3rd zinc concentrate and the 5th concentrate overall.

The remaining material in the cell is referred to as the tailing (tail).

The concentrates and tail were filtered, dried, weighted, and analyzed for Cu, Fe, and Zn. (For informational purposes the metal content of the various fractions was determined by the method of X-ray fluorescence spectrophotometry. A calibration cure for the X-ray was generated by analyzing some of the samples by atomic absorption spectrometry.)

The above procedure was repeated with the exception that 1,2-bis(methylthio) hexane was substituted and used as a direct replacement for both the 3418A and the SIPX.

The procedure was repeated a third time with the exception that 1,2-bis(methylthio) hexane was substituted and used as a direct replacement for the 3418A and the 1st addition of SIPX. The SIPX was not replaced in the final Zn flotation stage.

TABLE I

Cu—Zn Recovery Using 1,2-bis(methylthio) Hexane as a Collector

| | | | Copper Recovery | | | | | |
|---|---|---|---|---|---|---|---|---|
| Run | Concentrate 1 | Concentrate 2 | Cumulative 1 + 2 | Concentrate 3 | Concentrate 4 | Concentrate 5 | Tailing (Loss) | Cumulative 1 + 2 + 3 + 4 + 5 |
| 1 | 82.69 | 4.31 | 87.00 | 6.58 | 1.96 | 0.86 | 3.61 | 96.40 |
| 2 | 78.87 | 4.49 | 83.36 | 8.98 | 2.05 | 1.18 | 4.44 | 95.57 |
| 3 | 79.24 | 4.42 | 83.66 | 9.56 | 2.01 | 0.96 | 3.81 | 96.19 |

| | | | Zinc Recovery | | | | | |
|---|---|---|---|---|---|---|---|---|
| Run | Concentrate 1 | Concentrate 2 | Combined 1 + 2 | Concentrate 3 | Concentrate 4 | Concentrate 5 | Tailing (Loss) | Cumulative 1 + 2 + 3 + 4 + 5 |
| 1 | 14.94 | 8.16 | 23.10 | 71.50 | 3.75 | 0.40 | 1.26 | 98.75 |
| 2 | 11.05 | 5.40 | 16.45 | 75.13 | 5.48 | 1.39 | 1.56 | 98.45 |
| 3 | 11.29 | 5.33 | 16.62 | 79.21 | 2.34 | 0.50 | 1.32 | 98.67 |

| | | | Iron Recovery | | | | | |
|---|---|---|---|---|---|---|---|---|
| Run | Concentrate 1 | Concentrate 2 | Combined 1+2 | Concentrate 3 | Concentrate 4 | Concentrate 5 | Tailing (Loss) | Cumulative 1 + 2 + 3 + 4 + 5 |
| 1 | 11.05 | 9.93 | 20.98 | 22.84 | 15.80 | 8.06 | 32.31 | 67.68 |
| 2 | 7.18 | 7.34 | 14.52 | 23.22 | 6.50 | 6.79 | 48.98 | 51.03 |
| 3 | 7.39 | 6.95 | 14.34 | 33.08 | 9.17 | 13.61 | 29.80 | 70.20 |

| | Recovery of Zn Reporting to the Zn Flotation Stage | | | |
|---|---|---|---|---|
| Run | Concentrate 3 | Concentrate 4 | Concentrate 5 | Cumulative 3 + 4 + 5 |
| 1 | 92.97 | 4.88 | 0.52 | 98.37 |
| 2 | 89.92 | 6.56 | 1.66 | 98.14 |
| 3 | 95.00 | 2.81 | 0.60 | 98.41 |

There are two primary factors that are significant in evaluating the effectiveness of a collector. The first is whether it recovers the mineral of interest. The second is whether it rejects or at least does not promote the recovery of unwanted minerals. Unwanted minerals include those that are not of value and those that are recovered at the wrong time. Iron pyrite is an example of a mineral that most operations do not wish to recover. Sphalerite is an example of a mineral that is valuable and recovered but whose recovery is detrimental during the copper flotation stage.

The above example demonstrates the effectiveness of 1,2-bis(methylthio) hexane as mineral collector. It recovered both the copper and zinc minerals nearly as well as the control collectors in this ore sample. The total recovery of Cu and Zn were slightly below the control but still very good. Iron rejection was excellent and was superior to the control. Zn rejection in the copper flotation stage was also excellent and again superior to the control.

EXAMPLE II

This example illustrates the inventive process for preparing a bis(alkylthio) alkane in high yield.

The experiment was carried out in a 2-liter, 3-necked flask equipped with condenser, $N_2$ inlet, drying tube, stirring bar, and thermowell. The flask and a syringe were dried in an oven at 110° C. for ½ hour. Dimethyl disulfide (565 g; 6 moles) and 1-hexene (337 g; 4 moles) and catalytic quantity of boron trifluoride etherate (50 ml, using the syringe) were added to the flask. The reaction mixture was heated, with stirring, at 72°-80° C. for the length of time indicated in Table III below.

The reaction mixture, after cooling to ambient temperature, was transferred to a separatory funnel containing 700 ml of aqueous 10 weight percent NaOH solution. After shaking and upon phase separation, the aqueous phase was discarded and the organic phase was washed with 180 ml of water. The washed crude product was transferred to a distillation flask to isolate the desired product, 1,2-bis(methylthio) hexane by distillation at reduced pressure. The yield of the distilled product was 81% based on 1-hexene as the limiting reagent (run 1). In run 2, the yield was determined by gas chromatography (GC) analysis of the crude product. The GC analysis was carried out on a 20 in., 2% OV-101 column, initially at 50° C. with a programmed temperature rise of 15° C./min.

TABLE III

| Run No. | Heating Time (hr.) | Yield (%) |
|---|---|---|
| 1 | 13 | 81[a] |
| 2 | 12 | 88[b] |

[a]Yield based on distilled product with 1-hexene as limiting reagent.
[b]Yield determined by GC analysis of crude product.

EXAMPLE IIA

This example illustrates that comparable yield is obtainable with a different alkene as a reactant.

The run was the same as those shown in Example II with the exceptions that the reactants were dimethyl disulfide (394 g; 4.2 moles) and 1-octene (315 g; 2.8 moles) and the quantity of the catalyst was also decreased to 35 ml, and that the heating time (78°-82° C.) was 15 hours. After workup as in Example II and removal of unreacted disulfide and other lights by vacuum stripping, the crude product weighed 520.2 g. GC analysis as in Example II showed that 92% of the crude product was 1,2-bis(methylthio) octane. The reaction yield based on GC analysis was 83%.

The results of these two examples indicate that the invention is operable with different alkenes to achieve high yield of the desired products. Thus, the present invention is well adapted to carry out the objects and attain the ends and advantages mentioned as well as those inherent therein.

COMPARATIVE EXAMPLE II

This example illustrates that the use of an excess alkene in the reaction results in a very low yield of the desired product, compared to using an excess disulfide.

The experiment was carried out as those illustrated in Example II except that 1-hexene (673 g; 8.0 moles) was in excess relative the disulfide (377 g or 4.0 moles), the total catalyst used was increased to 68 ml, and the heating time was 20 hours. This reaction resulted in 38% yield (distilled) of 1,2-bis(methylthio) hexane.

COMPARATIVE EXAMPLE IIA

This example further demonstrates that the thiolating agent (the disulfide) must be in excess.

The experiment was carried out the same as those described in Example II except that equimolar quantities of reactants (471 g or 5.0 moles of dimethyl disulfide and 421 g or 5.0 moles of 1-hexene) were used. The equimolar reactant resulted in only 49% yield (distilled).

These examples indicate that the inventive method using excess disulfide is a superior method to that using excess alkene suggested by the J. Org. Chem. 50:4390 (1985) reference for preparing a bis(organothio) alkane.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

That which is claimed is:

1. A process for preparing a bis(organothio) alkane having the formula of RCH(SR″)CH(SR″)R′ comprising contacting an alkene having the formula of RCH═CHR′ with an amount of a thiolating agent having the formula of R″SSR″ in the presence of a catalyst, wherein said amount is from about 1.2 to about 10.0 in terms of mole ratio of said thiolating agent to said alkene, wherein said catalyst is selected from the group consisting of boron trichloride, boron tribromide, boron trifluoride, aluminum chloride, and a boron trifluoride dialkyl etherate. and wherein R is an alkyl group having 1 to 20 carbon atoms, R′ is hydrogen and R″ is an alkyl or aryl group having 1 to 10 carbon atoms.

2. A process according to claim 1 wherein said bis(organothio) alkane is a bis(alkylthio) alkane having the formula of RCH(SR″)CH(SR″)R′ wherein R is an alkyl group having 1 to 20 carbon atoms, R′ is hydrogen and R″ is an alkyl group having 1 to 10 carbon atoms.

3. A process according to claim 2 wherein said bis(alkylthio) alkane is 1,2-bis(methylthio) hexane.

4. A process according to claim 2 wherein said bis(alkylthio) alkane is 1,2-bis(methylthio) octane.

5. A process according to claim 1 wherein said bis(organothio) alkane is a bis(arylthio) alkane having the formula of RCH(SR″)CH(SR″)R′ wherein R is an alkyl group having 1 to 20 carbon atoms, R′ is hydrogen and R″ is an aryl group having 6 to 10 carbon atoms.

6. A process according to claim 5 wherein said aryl group is unsubstituted or substituted with one or more substituents selected from the group consisting of $C_1$-$C_4$ alkyl, halo and $OR_1$, and wherein $R_1$ is $C_1$-$C_4$ alkyl.

7. A process according to claim 5 wherein R and R′ are selected from the group consisting of $C_1$-$C_4$ alkyl, halo, $OR_1$, and mixtures thereof, and wherein $R_1$ is a $C_1$–$C_4$ alkyl.

8. A process according to claim 1 wherein said bis(organothio) alkane is a bis(alkylthio) alkane; said alkene is a 1-alkene; said thiolating agent is a dialkyl disulfide; and said catalyst is a boron trifluoride dialkyl etherate.

9. A process according to claim 1 wherein said bis(organothio) alkane is a bis(arylthio) alkane; said alkene is a 1-alkene; said thiolating agent is a diaryl disulfide; and said catalyst is a boron trifluoride dialkyl etherate.

10. A process according to claim 8 wherein said bis-(alkylthio) alkane is 1,2-bis(methylthio) hexene; said 1-alkene is 1-hexene; said dialkyl disulfide is dimethyl disulfide; and said boron trifluoride dialkyl etherate is boron trifluoride diethyl etherate.

11. A process according to claim 1 wherein said mole ratio ranges from about 1.5 to about 3.0.

12. A process according to claim 1 wherein said contacting is carried out at a temperature range of from about 20° C. to about 150° C.

13. A process according to claim 12 wherein said temperature range is from 50° C. to 100° C.

14. A process according to claim 1 wherein said contacting is carried out under a pressure range of from about 1 to about 5 atms.

15. A process for preparing 1,2-bis(methylthio) hexane comprising contacting 1-hexene with an amount of dimethyl disulfide in the presence of a catalytic amount of boron trifluoride diethyl etherate, wherein said amount is from about 1.2 to about 10.0 in terms of mole ratio of said dimethyl disulfide to said 1-hexene.

16. A process according to claim 15 wherein said dimethyl disulfide is present in the range of from about 1.5 to about 3.0 in terms of molar ratio of said dimethyl disulfide to said 1-hexene; and said contacting is carried out at 50° C. to 100° C. under about 1 to about 5 atms.

17. A process for preparing 1,2-bis(methylthio) octane comprising contacting 1-octene with an amount of dimethyl disulfide in the presence of a catalytic amount of boron trifluoride diethyl etherate, wherein said amount is from about 1.0 to about 10.0 in terms of mole ratio of said dimethyl disulfide to said 1-octene.

18. A process according to claim 17 wherein said dimethyl disulfide is present in the range of from about 1.5 to about 3.0 in terms of molar ratio of said dimethyl disulfide to said 1-octene; and said contacting is carried out at 50° C. to 100° C. under about 1 to about 5 atms.

* * * * *